United States Patent [19]

Yli-Urpo et al.

[11] Patent Number: 5,762,950
[45] Date of Patent: Jun. 9, 1998

[54] BIOCERAMIC SYSTEM FOR DELIVERY OF BIOACTIVE COMPOUNDS

[75] Inventors: Antti Yli-Urpo, Littoinen; Harry Gösta Jalonen; Kauko Oiva Antero Kurkela, both of Turku, all of Finland

[73] Assignee: Orion-Yhtymä Oy, Espoo, Finland

[21] Appl. No.: 438,557

[22] Filed: May 10, 1995

Related U.S. Application Data

[62] Division of Ser. No. 958,104, filed as PCT/FI91/00196, Jun. 24, 1991, abandoned.

[30] Foreign Application Priority Data

Jun. 25, 1990 [GB] United Kingdom .................. 9014052

[51] Int. Cl.⁶ .................. A61F 1/00; A61K 9/00
[52] U.S. Cl. .................. 424/422; 424/426; 424/464; 424/468; 424/469; 424/484; 501/1; 501/11; 501/17; 501/32; 501/53; 501/55; 501/63; 501/72; 264/56
[58] Field of Search .................. 424/422, 426, 424/464, 468, 469, 484; 501/1, 11, 17, 32, 53, 55, 63, 72; 264/56

[56] References Cited

U.S. PATENT DOCUMENTS

| | | | |
|---|---|---|---|
| 4,131,597 | 12/1978 | Blüethgen et al. | 260/42.18 |
| 4,135,935 | 1/1979 | Pfeil et al. | 106/35 |
| 4,146,936 | 4/1979 | Aoyagi et al. | 3/1.91 |
| 4,334,029 | 6/1982 | Naito et al. | 501/109 |
| 4,655,777 | 4/1987 | Dunn et al. | 623/16 |
| 4,708,652 | 11/1987 | Fujiu et al. | 433/201.1 |
| 4,783,429 | 11/1988 | Shibuya et al. | 501/5 |
| 4,960,426 | 10/1990 | Atsumi | 623/16 |
| 4,994,414 | 2/1991 | Yamamoto et al. | 501/12 |
| 5,010,042 | 4/1991 | Kandachi | 501/32 |
| 5,068,122 | 11/1991 | Kokubo et al. | 427/2 |
| 5,074,916 | 12/1991 | Hench et al. | 106/35 |
| 5,120,340 | 6/1992 | Ducheyne et al. | 35/18.3 |
| 5,232,878 | 8/1993 | Kasuga et al. | 501/10 |
| 5,262,166 | 11/1993 | Liu et al. | 424/423 |
| 5,318,929 | 6/1994 | Jana et al. | 501/10 |
| 5,356,436 | 10/1994 | Nonami et al. | 623/16 |
| 5,364,839 | 11/1994 | Gerhart et al. | 514/12 |

FOREIGN PATENT DOCUMENTS

| | | |
|---|---|---|
| 0 147 932 | 7/1985 | European Pat. Off. |
| 0 302 847 | 2/1989 | European Pat. Off. |
| 101145 | 6/1984 | Japan |
| 59-101145 | 6/1984 | Japan |
| 1-265969 | 10/1989 | Japan |
| 1-275765 | 11/1989 | Japan |
| 1 493 749 | 11/1977 | Switzerland |
| WO 87/00058 | 1/1987 | WIPO |
| WO 91/12212 | 8/1991 | WIPO |

OTHER PUBLICATIONS

Dialog file 351, World Patents Index, English Abstract (Derwent) of Japanese Patent Publication No. 59101145 (Reference AN1).

Dialog File 351, World Patents Index, English Abstract (Derwent) of PCT Publication No. WO 87/00058 (Reference AP1).

*Primary Examiner*—Frederick Krass
*Attorney, Agent, or Firm*—Sterne, Kessler, Goldstein & Fox P.L.L.C.

[57] ABSTRACT

A bioceramic system for delivery of a bioactive compound, which comprises a combination of bioactive glass, bioactive glass ceramic or bioactive ceramic, hydroxyapatite, optionally one or more other calcium phosphate compound and optionally a matrix, and which may incorporate into the bioceramic system a bioactive compound. The timing of the release of the bioactive compound can be regulated as desired and depends on the conditions of the surrounding, the composition of the bioceramic system and its method preparation.

69 Claims, 12 Drawing Sheets

A = BIOACTIVE REGION (BIOACTIVE GLASS, BIOACTIVE GLASS CERAMIC AND BIOACTIVE CERAMIC)
B = INERT REGION
C = SOLUBLE GLASS
D = GLASS IS NOT FORMED

FIG. 12

BIOCERAMIC SYSTEM FOR DELIVERY OF BIOACTIVE COMPOUNDS

This application is a division of application Ser. No. 07/958,104, filed Jan. 29, 1993, now abandoned which is a 371 of PCT/FI91/00196 filed Jun. 24, 1991.

The present invention relates to a bioceramic system for controlled delivery of bioactive compounds such as medicines, proteins, hormones etc.. The present invention also relates to pharmaceutical preparations comprising the bioceramic system, and a process for preparing the system. The bioceramic system comprises wholly or partly of a combination of bioactive glass, bioactive glass ceramic or bioactive ceramic, and hydroxyapatite. In addition to hydroxyapatite the system may contain one or more other calcium phosphate compounds, such as rhenanite or tricalcium phosphate. The system may also contain a matrix.

Bioactive glass, glass ceramic or ceramic is a ternary mixture of $SiO_2$, $Na_2O$ and $CaO$, which sinters to glass, glass ceramic or ceramic. Relative proportions of these three components which result in a mixture which is bioactive are included in the bioactive region illustrated in FIG. 1 The components $SiO_2$, $Na_2O$ and $CaO$ form the basis of the bioactive glass, glass ceramic or ceramic. The mixture may contain other components, such as $P_2O_5$, $Al_2O_3$ or $B_2O_3$ or other metallic or non-metallic oxides. Bioactive glass, glass ceramic or ceramic reacts with water or tissue fluid by forming a reactive silica-rich layer and a layer rich in calcium and, if present, phosphorous. This reaction does not irritate the tissue in which the bioceramic system is implanted so that no inflammation reaction will develop. Bioactive glass is amorphous, bioactive glass ceramic has crystalline or ceramic particles in the amorphous glass and bioactive ceramic is crystalline.

Bioceramics which consist of wholly water soluble glass compositions are known for example as implants and oral formulations for liberating active compounds at a controlled rate (EP 147932). On the other hand implants made of hydroxyapatite are known to be used for delivering active materials (JP 101145/1984). Muscle tissue has been found to be firmly connected to hydroxyapatite by fibrous tissue and those adhered firmly to each other (S. Negami et al. Abstract World Congress of High Tech Ceramics, Milan, 1986). This means that hydroxyapatite implants do not disappear from soft tissue.

It has now been found that by combining hydroxyapatite with bioactive glass, glass ceramic or ceramic, the activity of which can be regulated, a bioceramic system is produced the resorption rate of which is regulatable and distinguishes from the resorption rate of the pure bioactive glass, glass ceramic or ceramic component.

Thus the present invention provides a bioceramic system for delivery of a bioactive compound which comprises hydroxyapatite and bioactive glass, bioactive glass ceramic or bioactive ceramic.

The bioceramic system according to the invention resorbs completely and dissappears from soft tissue even though it contains hydroxyapatite. When hydroxyapatite is combined with bioactive glass, glass ceramic or ceramic an interphase reaction starts and reactive interphases are formed. The bioceramic system may be made by sintering the combination of ingredients or pressing the ingredients into shape. The interphase reaction is activated by high temperatures used during sintering or by an electrolyte e.g. water which may be used when tablets are made by pressing at room temperature. The reactive interphases may be regulated e.g. by changing the amount of hydroxyapatite. The reactive interphases are not formed if the above mentioned combination is not made and the unique properties of the present bioceramic system as mentioned above, are due to the presence of these interphases.

The bioceramic system may also contain one or more other calcium phosphate compounds, such as rhenanite or tricalciumphosphate.

The bioceramic system may also comprise wholly or partly of a combination of hydroxyapatite and two or more of a bioactive glass, bioactive glass ceramic and bioactive ceramic.

Figure 1:
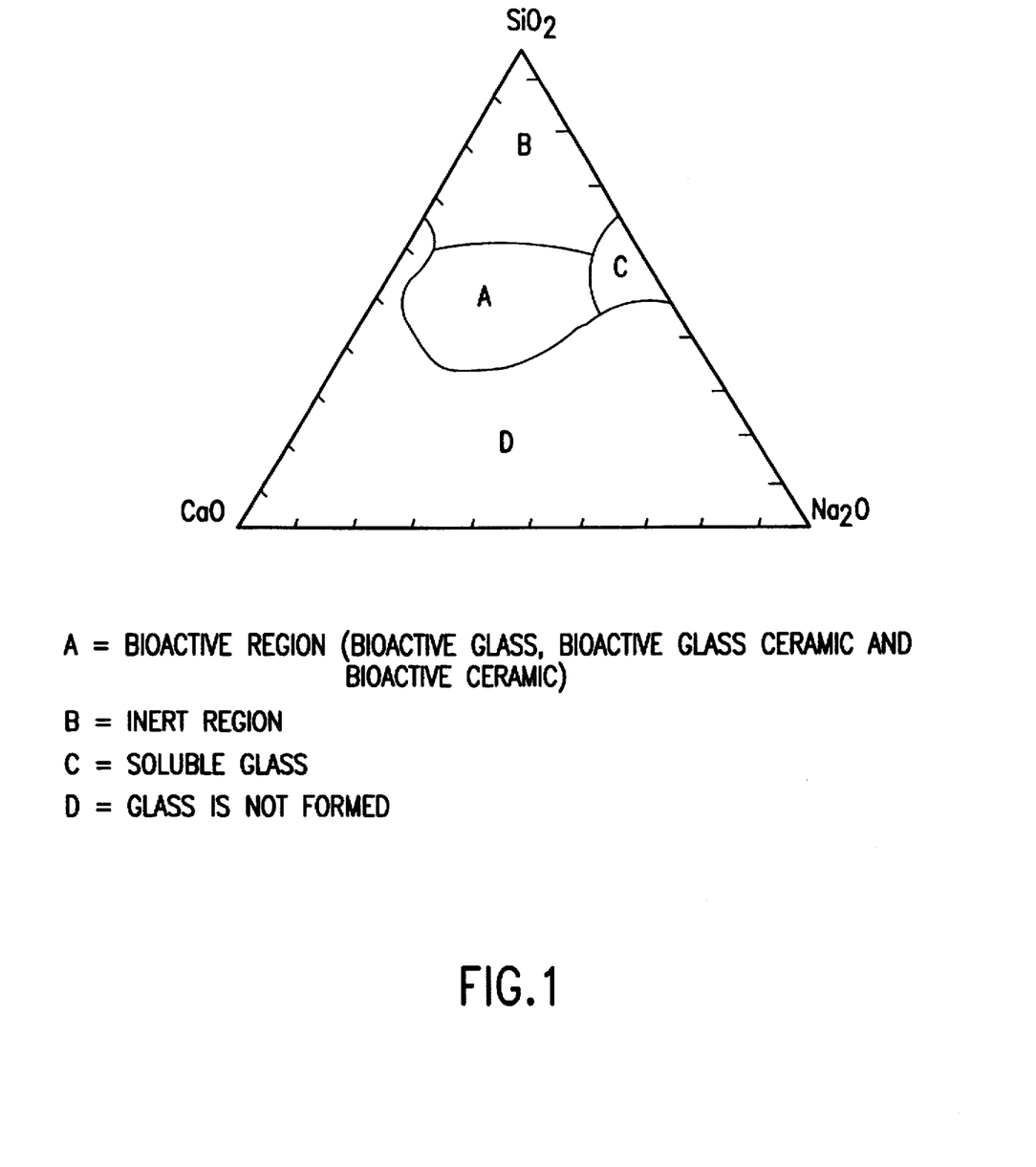
FIG. 1 Bioactive region showing the relative proportions of $SiO_2$, $Na_2O$ and $CaO$ which result in a mixture which is bioactive.

Bioactive glass, glass ceramic or ceramic which may be used in this system are any mixture comprising the three components $SiO_2$, $Na_2O$ and $CaO$ in the relative proportions within the region A shown in FIG. 1, and which sinter to give glass, glass ceramic or ceramic.

The hydroxyapatite used in the bioceramic system may be synthesized using methods known in the art. If, as is generally the case, the bioceramic system is to be used in a pharmaceutical preparation, the hydroxyapatite should be of a quality acceptable for this use.

The effect of hydroxyapatite, and thus the effect of the interphase, is dependent on the pH of the surrounding fluid. At low pH-values generally an increasing amount of hydroxyapatite in the bioceramic system increases the resorption rate. Especially increasing the amount of hydroxyapatite from about 10% to about 70% in the bioceramic system made by pressing increases the resorption rate at pH 1.2 and in the bioceramic system made by sintering the hydroxyapatite increase from about 30% to about 70% increases the resorption rate at pH 1.2. At high pH-values the effect is as follows: first increasing amounts of hydroxyapatite in the bioceramic system lead to decreasing resorption rate but then increasing amounts of hydroxyapatite increase the resorption rate. There is an amount of hydroxyapatite where the resorption rate is at its minimimium. It may be estimated that the resorption rate of the bioceramic system, which consists of bioactive glass, hydroxyapatite and water as matrix, made by pressing or sintering is at its minimum when the amount of hydroxyapatite in the system is from about 10% to about 50%. The region where the minimum resorption rate is achieved is dependent on e.g. the temperature used when sintering, the number of pores in the system, the matrix and the nature of the bioactive compound.

Medical preparations for oral use decompose in variable pH (pH≈1–7.5); preparations such as implants decompose in approximately neutral pH surrounding. The combination of hydroxyapatite with bioactive glass, glass ceramic or ceramic can be used to obtain oral preparations which resorb more rapidly in stomach than if bioactive glass, glass ceramic or ceramic alone has been used. The combination of hydroxyapatite with bioactive glass, glass ceramic or ceramic provides an implant which resorbs more slowly or more quickly than if bioactive glass, glass ceramic or ceramic alone is used.

The matrix material which may be used in the bioceramic system may be water, waterglass or any non-toxic polymer or similar compound. The polymer can be a natural polymer, such as gelatine, or a synthetic polymer, such as polyacrylic acid, polymaleic acid, polylactic acid, polytartaric acid or polyglycolic acid.

The bioceramic system may contain one or more bioactive compound. The bioactive compounds which may be delivered using the bioceramic system may be e.g. medicines, proteins or hormones. The suitable bioactive compounds may be e.g. anti-infectives (e.g. antibiotics and antiviral agents), analgesics and analgesic combinations, anorexics, antihelminthics, parasiticides, antiartritics, antiasthmatic agents, anticonvulsants, antidepressants, antidiabetic agents, antidiarrheals, antihistamines, antiinflammatory agents, antimigraine preparations, antinauseants, antineoplastics, anticancer agents (e.g. methotrexate), antipruritics, antpsychotics, antipyretics, antispasmodics, anticholinergics, sympathomimetics, xanthine derivatives, cardiovascular preparations, antiarrythmics, antihypertensives, diuretics, vasodilators, CNS(=central nervous system) drugs such as antiparkinsonism drugs (e.g. selegiline), cough and cold preparations, decongestants, estradiol and other steroids, contraceptives, prophylactic agents, hypnotics, immunosuppressives, muscle relaxants, parasympatholytics, psychostimularilts, sedatives (e.g. atipamezole), tranquilizers and cognitive dysfunction drugs. The bioactive compounds suitable for delivery by a bioceramic system may also be nutrients, fertilisers, herbicides, insecticides, pheromones, molluscides, larvicides, nematocides, fungicides, algicides, slimicides or rodenticides. The system may be used to deliver compounds which are unstable or poorly soluble in simple aqueous solutions. Compounds which it is desirable to administer to only a restricted area may also be delivered using the bioceramic system, preferably as an implant. The system may be designed to allow slow release of a compound.

The surface of the bioceramic system reacts instantly with its surrounding in living tissue, tissue fluid or in aqueous solution, which leads to resorption the time of which depends on the composition. The resorption can be regulated by changing the ratio of hydroxyapatite and bioactive glass, glass ceramic or ceramic and, if present, other calcium phosphate compound(s) and the matrix. The release of the bioactive material from the bioceramic system can be restrainedly regulated based on the phenomenon described above. For instance by changing the amount of hydroxyapatite in the bioceramic system the timing of the release of the bioactive compound can be regulated as desired and depends on the conditions of the surroundings, the method of preparation of the bioceramic system, the composition of the bioceramic system or the nature of the bioactive compound.

The bioceramic system incorporating a bioactive compound, may be administered to a human or animal patient orally, by implanting into tissue in various ways or it may act by releasing a bioactive compound through mucous membrane. The bioceramic system may be used in various forms such as a monolithe, multi-particle system, whiskers-like or fibrous system, tablet, pill, granule, suppository or suspension. The bioceramic system may be attached to e.g. a tooth; it may also be implanted or connected into plant tissue.

The structure of the bioceramic system may be based on a single or multi layer system, a homogenic material or a combination of particles of different type and/or size. The bioceramic system may also be coated with matrix The bioceramic system containing a bioactive compound may be administered to a subject in an amount sufficient to release the desired amount of bioactive compound at a particular time or at a particular rate. For a known medicine the desired dose can be calculated and the bioceramic system can be produced which will release the desired dose under the ambient conditions resulting from its administration to the subject.

The bioceramic system may be prepared by combining ground and sieved bioactive glass, glass ceramic or ceramic, hydroxyapatite and, if present, matrix and pressing, e.g. forming a tablet using a mold. The bioactive compound may be combined with the components of the bioceramic system before molding or the bioactive compound may be impregnated in the tablet after molding. The bioceramic system may also be prepared by sintering a combination of bioactive glass, glass ceramic or ceramic, hydroxyapatite and optionally a little amount of matrix e.g. water. The bioceramic system made by sintering is then impregnated with a bioactive compound. In the examples used to illustrate the invention the bioactive glass used for sample preparation was ground in a ball mill and sieved. The fraction under 53 micrometers was used. The bioactive glass used in the examples was a mixture of $SiO_2$ (52.7 w-%), $Na_2O$ (20.75w-%), CaO (15.60 w-%), $P_2O_5$ (6.8 w-%), $Al_2O_3$ (0.8 w-%) and $B_2O_3$ (3.3 w-%) except in Experiment 7 where the bioactive glass was a mixture of $SiO_2$ (55.26 mol-%), $Na_2O$ (26.21 mol-%), CaO (12.01 mol-%), $P_2O_5$ (2.4 mol-%), $Al_2O_3$ (1.24 mol-%) and $B_2O_3$ (2.9 mol-%). The hydroxyapatite used was specially synthesized and pure. The fraction under 100 micrometers was used. The water glass used was of normal technical grade- Gelatine was used as matrix either as a dry powder or as a gel.

For preparing the samples two different methods of tablet preparation were used depending on the consistency of the wet mixture. The more solid mixtures were pressed into tablets in a press normally used for making tablets for IR-analysis. The content of the bioactive compound was 1 wt-%. The tablets were kept under constant pressure in the press for 1 minute.

Further two different methods were used when preparing samples containing gelatine. The first method consisted of mixing the solid components with solid gelatine followed by moistening this mixture in the tablet press with a few drops of water. This method gave good solid tablets. In the second method the gelatine was mixed with water to form a 2% solution. The gelatine was allowed to dissolve by letting the mixture stand overnight. This solution was then used as matrix when pressing the tablets. An extruder method may also be used.

The samples that were too liquid to be pressed were molded using a plate of silicon rubber with cylindrical holes. The mixture was spread in the mold. The tablets were allowed to harden before they were removed from the mold. The tablets prepared by this technique varied somewhat in size. Since the bioactive compound was mixed with the ingredients of the bioceramic system before molding, the content of the bioactive compound was constant the exact amount of the bioactive compound could be calculated for each tablet from its total weight.

The samples that were sintered were first pressed except in Experiment 7 where the samples were not pressed before sintering. The sintering was performed in 650° C. for 10 minutes (in Experiment 73 min at 930° C. and 6 min at above 730° C.).

The methods described above to prepare the samples are illustrative and are not intended to be restricting. The following experiments illustrate the invention. All the experiments except Experiment 7 were carried out in room temperature.

The samples were analyzed with Hewlett-Packard 1081 B liquid chromatograph.

EXPERIMENT 1

It is shown in Table 1 that the increase of the amount of hydroxyapatite decreases the released amount of selegiline hydrochloride when the time is constant. The experiment was carried out in phosphate buffer pH 7.4 (USP). Each tablet contained 20 mg of selegiline hydrochloride and they were made by pressing. The dissolution was carried out by shaking with hands a few seconds once a day.

TABLE 1

The amount of selegiline hydrochloride released from the total amount (%) in 15 days when the ratio of hydroxyapatite (HA) is changed.

| No. | bioactive glass/% | HA/% | gelatine/% | selegiline released/% |
|---|---|---|---|---|
| 1 | 88 | 10 | 2 | 59 |
| 2 | 68 | 30 | 2 | 37 |
| 3 | 28 | 70 | 2 | 16 |

EXPERIMENT 2

Figure 2:
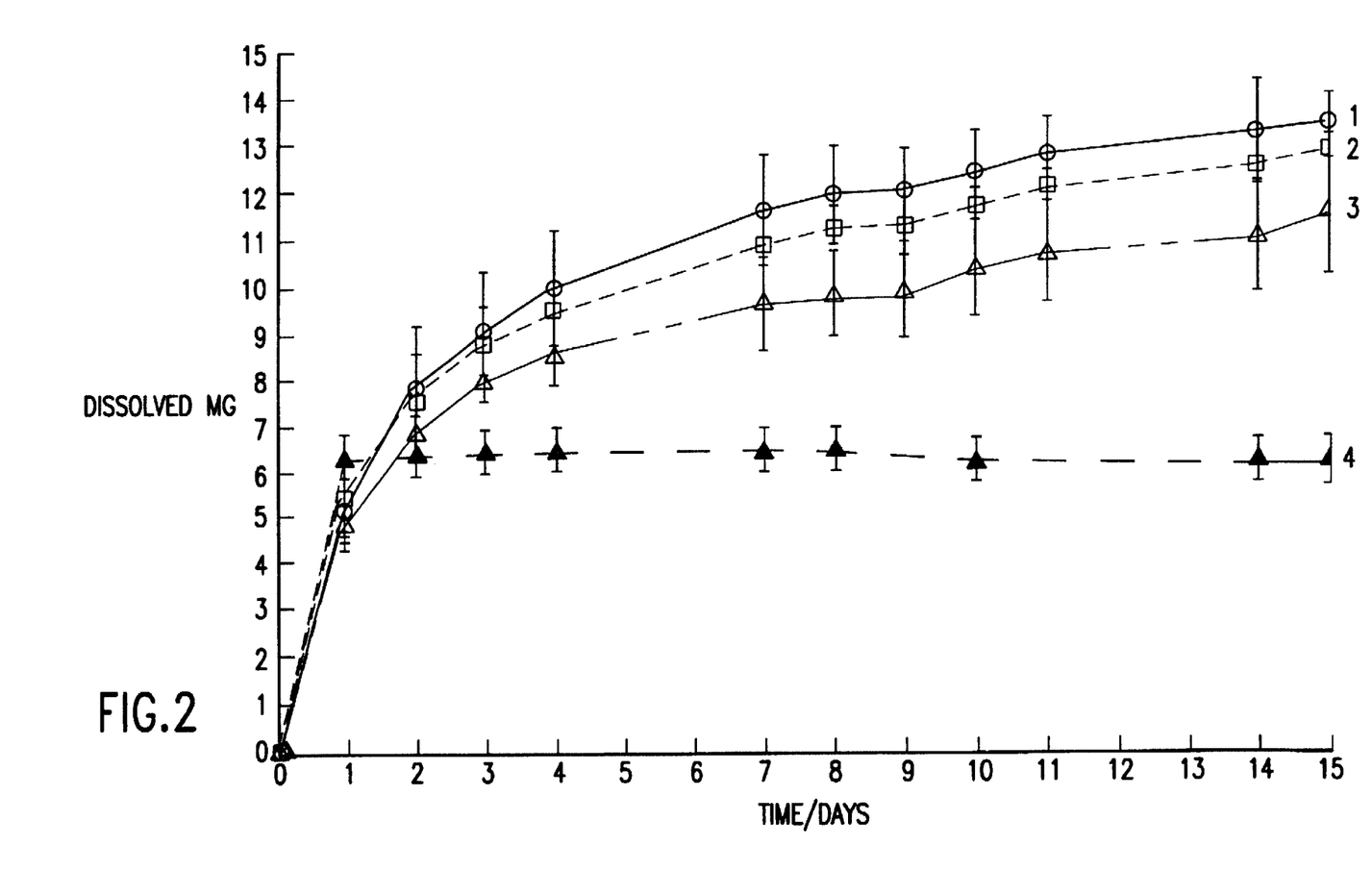
FIG. 2 The dissolution of selegiline hydrochloride as a function of time in phosphate buffer pH 7.4 (USP) from tablets comprising selegiline hydrochloride powder and the components of the bioceramic system. The selegiline hydrochloride powder was mixed with the components of the bioceramic system before pressing. Each tablet contained about 18 mg of selegiline hydrochloride. The components of the bioceramic system are presented in Table 2.

The dissolution of selegiline hydrochloride as a function time in phosphate buffer pH 7.4 (USP) is presented in FIG. 2. The selegiline hydrochloride powder was mixed with the components of the bioceramic system before pressing. Each tablet contained about 18 mg of selegiline hydrochloride. The components of the system are presented Table 2. The dissolution was carried out as described in Experiment 1.

TABLE 2

| No. | bioactive glass/% | HA/% | $H_2O$ |
|---|---|---|---|
| 1 | 100 | 0 | 2–4 drops |
| 2 | 95 | 5 | 2–4 drops |
| 3 | 50 | 10 | 2–4 drops |
| 4 | 50 | 50 | 2–4 drops |

EXPERIMENT 3

Figure 3:
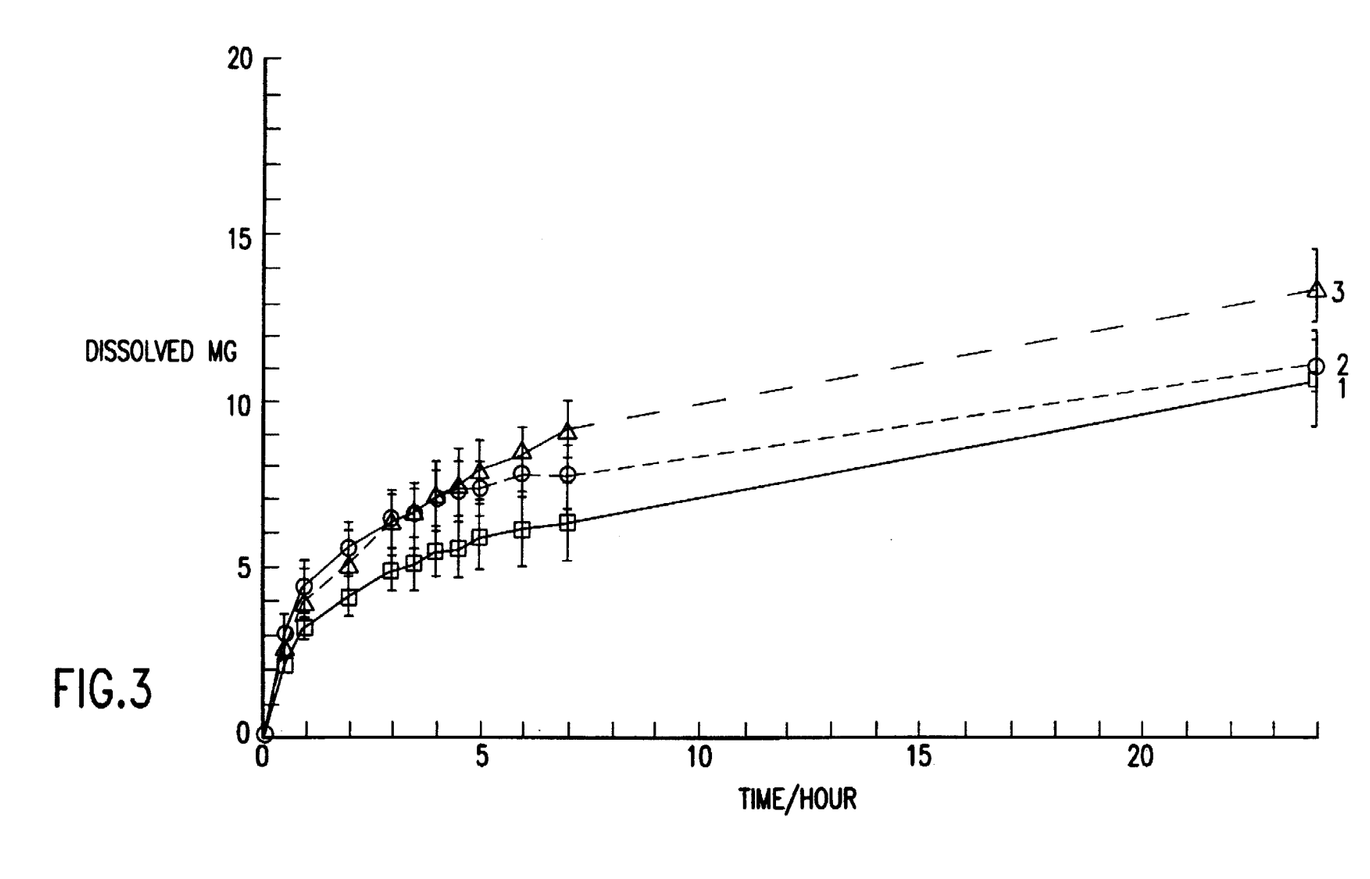
FIG. 3 The dissolution of selegiline hydrochloride as a function of time in pH 1.2 (0.1M hydrochloric acid) from tablets comprising selegiline hydrochloride and the components of the bioceramnic system. The tablets were pressed and the components of the bioceramic system are presented in Table 3. Each tablet contained about 15 mg of selegiline hydrochloride.

The dissolution of selegiline hydrochloride as a function of time in pH 1.2 (0.1M hydrochloric acid) is presented in FIG. 3. The tablets were pressed and the contents of the bioceramic system are presented in Table 3. Each tablet contained about 15 mg of selegiline hydrochloride. The dissolution was carried out by shaking in a linear shaker with the speed 110/min.

TABLE 3

| No. | bioactive glass/% | HA/% | gelatine/% | $H_2O$ |
|---|---|---|---|---|
| 1 | 88 | 10 | 2 | 2–4 drops |
| 2 | 68 | 30 | 2 | 2–4 drops |
| 3 | 28 | 70 | 2 | 2–4 drops |

EXPERIMENT 4

Figure 4:
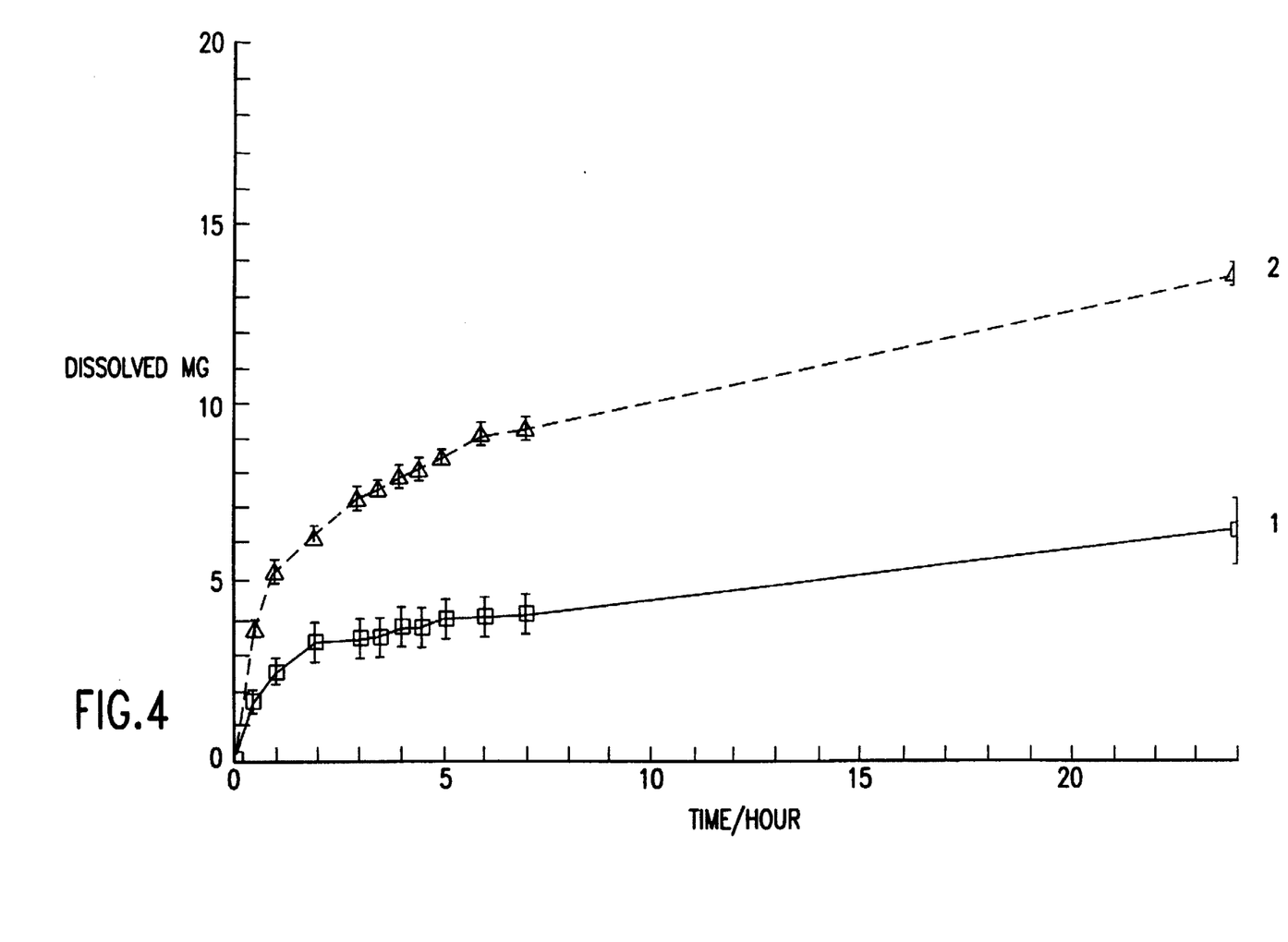
FIG. 4 The dissolution of selegiline hydrochloride as a function of time in pH 1.2 (0.1M hydrochloric acid) from tablets comprising selegiline hydrochloride and the components of the bioceramic system. The tablets were made by molding. The components of the bioceramic system are presented in Table 4. Each tablet contained about 15 mg of selegiline hydrochloride.

The dissolution of selegiline hydrochloride as a function of time in pH 1.2 (0.1M hydrochloric acid) is presented in FIG. 4. The tablets were made by molding and the components of the bioceramic system are presented in Table 4. Each tablet contained about 15 mg of selegiline hydrochloride. The dissolution was carried out as described in Experiment 3.

TABLE 4

| No. | bioactive glass/% | HA/% | waterglass/% |
|---|---|---|---|
| 1 | 80 | 10 | 10 |
| 2 | 20 | 70 | 10 |

EXPERIMENT 5

Figure 5:
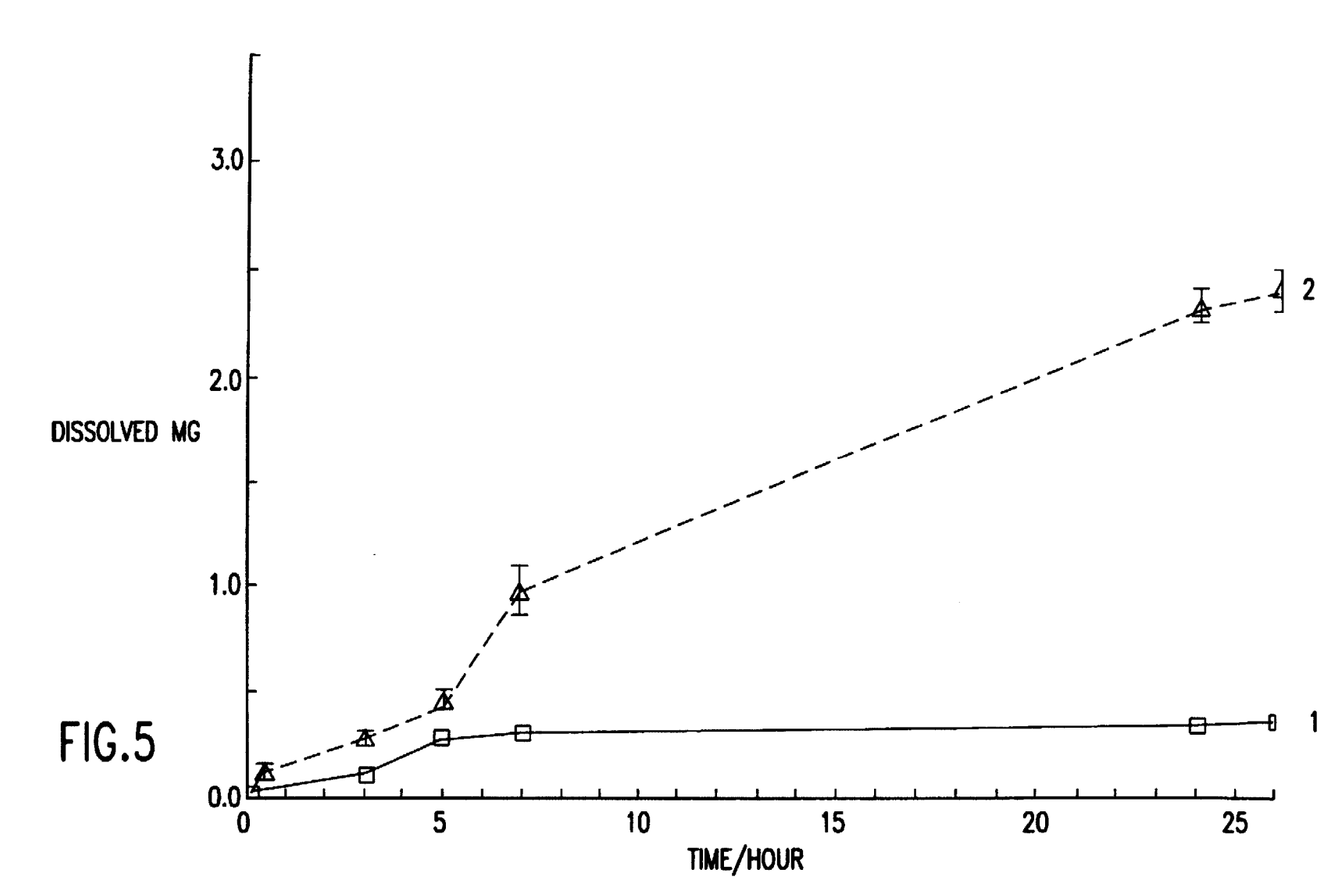
FIG. 5 The dissolution of nifedipine as a function of time in pH 1.2 (0.1M hydrochloric acid) from tablets comprising nifedipine and the components of the bioceramic system. The tablets were made by pressing. The components of the bioceramic system are presented in Table 5. Each tablet contained about 5 mg of nifedipine.

The dissolution of nifedipine as a function of time in pH 1.2 (0.1M hydrochloric acid) is presented in FIG. 5. The tablets were made by pressing and the components of the bioceramic system are presented in Table 5. Each tablet contained about 5 mg of nifedipine. The dissolution was carried out as described in Experiment 3.

TABLE 5

| No. | bioactive glass/% | HA/% | gelatine/% |
|---|---|---|---|
| 1 | 88 | 10 | 2 |
| 2 | 28 | 70 | 2 |

EXPERIMENT 6

Figure 6:
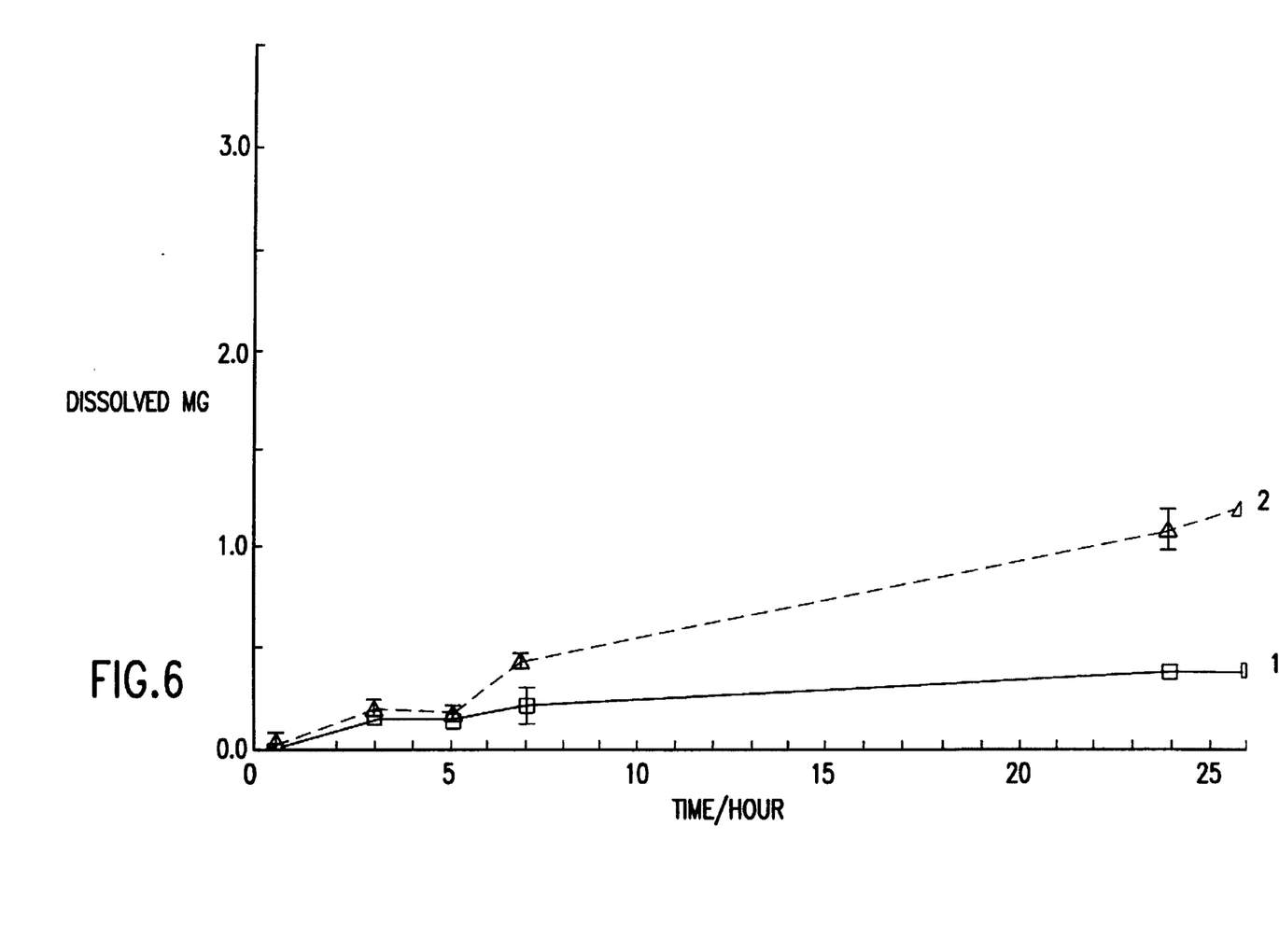
FIG. 6 The dissolution of nifedipine as a function of time in pH 1.2 (0.1M hydrochloric acid) from tablets comprising nifedipine and the components of the bioceramic system. The tablets were made by molding. The components of the bioceramic system are presented in Table 6. Each tablet contained approximately 4 mg of nifedipine.

The dissolution of nifedipine as a function of time in pH 1.2 (0.1M hydrochloric acid) is presented in FIG. 6. The tablets were made by molding and the components of the bioceramic system are presented in Table 6. Each tablet contained about 4 mg of nifedipine. The dissolution was carried out as described in Experiment 3.

TABLE 6

| No. | bioactive glass/% | HA/% | waterglass/% |
|---|---|---|---|
| 1 | 80 | 10 | 10 |
| 2 | 20 | 70 | 10 |

EXPERIMENT 7

Figure 7:
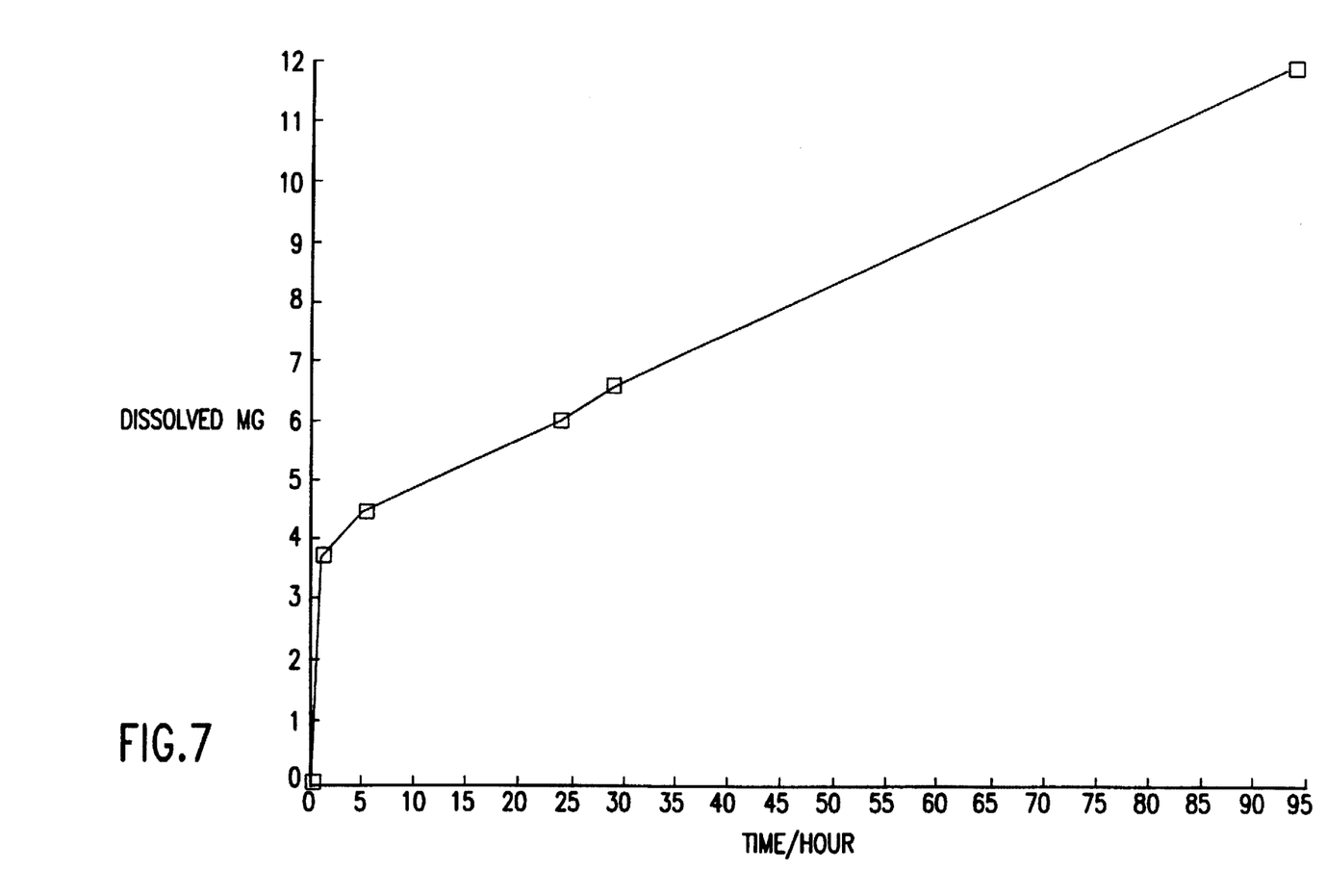
FIG. 7 The dissolution of methotrexate as a function of time in water from tablets comprising methotrexate and the components of the bioceramic system. The bioceramic system, which consisted of 50% bioactive glass and 50% hydroxyapatite was sintered at 930° C. for 3 min. and above 730° C. for 6 min and subsequently impregnated with methotrexate solution. Each tablet contained about 10 mg of methotrexate.

The dissolution of methotrexate as a function of time in water is presented in FIG. 7. The bioceramic system which consisted of 50% of bioactive glass and 50% of hydroxyapatite was sintered at 930° C. for 3 min and above 730° C for 6 min and after that impregnated with methotrexate solution. The tablet contained about 10 mg of methotrexate. The dissolution was carried out by a dissolution method with baskets according to USP (50 rpm, 37° C.).

EXPERIMENT 8

Figure 8:
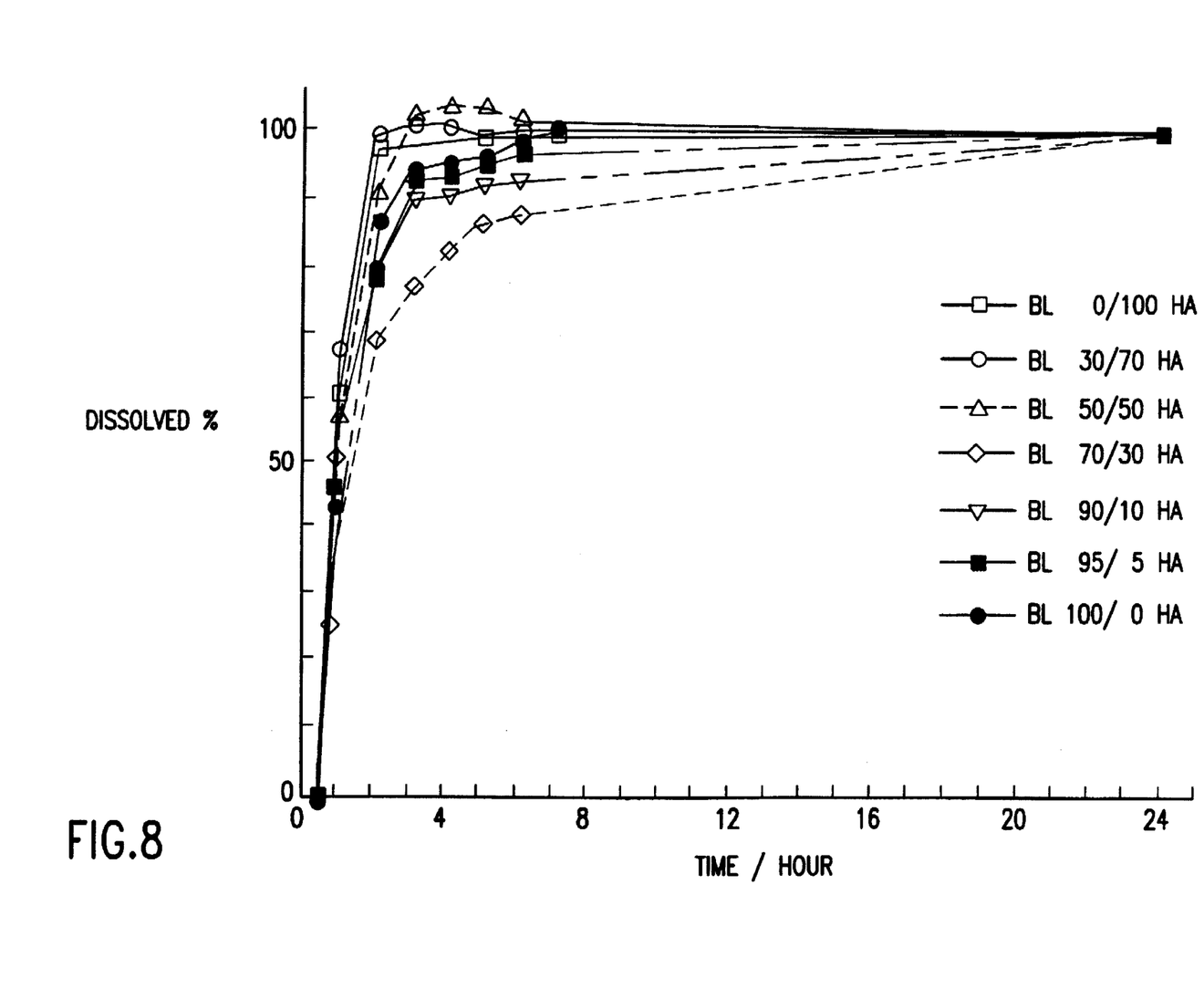
FIG. 8 The dissolution of selegiline hydrochloride as a function of time in pH 1.2 (0.1M hydrochloric acid) from tablets comprising selegiline hydrochloride and the components of the bioceramic system. The tablets were pressed and then sintered. The tablets were impregnated with selegiline hydrochloride solution so that each tablet contained about 20 mg of the active compound. The components of the bioceramic system are presented in Table 7.

The dissolution of selegiline hydrochloride as a function of time in pH 1.2 (0.1M hydrochloric acid) is presented in FIG. 8. The tablets were pressed and then sintered. The tablets were impregnated with selegiline hydrochloride solution so that each tablet contained about 20 mg of the active compound. The components of the bioceramic system are presented in Table 7. The dissolution was carried out as described in Experiment 3.

TABLE 7

| No. | bioactive glass/% | HA/% |
|---|---|---|
| 1 | 0 | 100 |
| 2 | 30 | 70 |
| 3 | 50 | 50 |
| 4 | 70 | 30 |
| 5 | 90 | 10 |
| 6 | 95 | 5 |
| 7 | 100 | 0 |

EXPERIMENT 9

Figure 9:
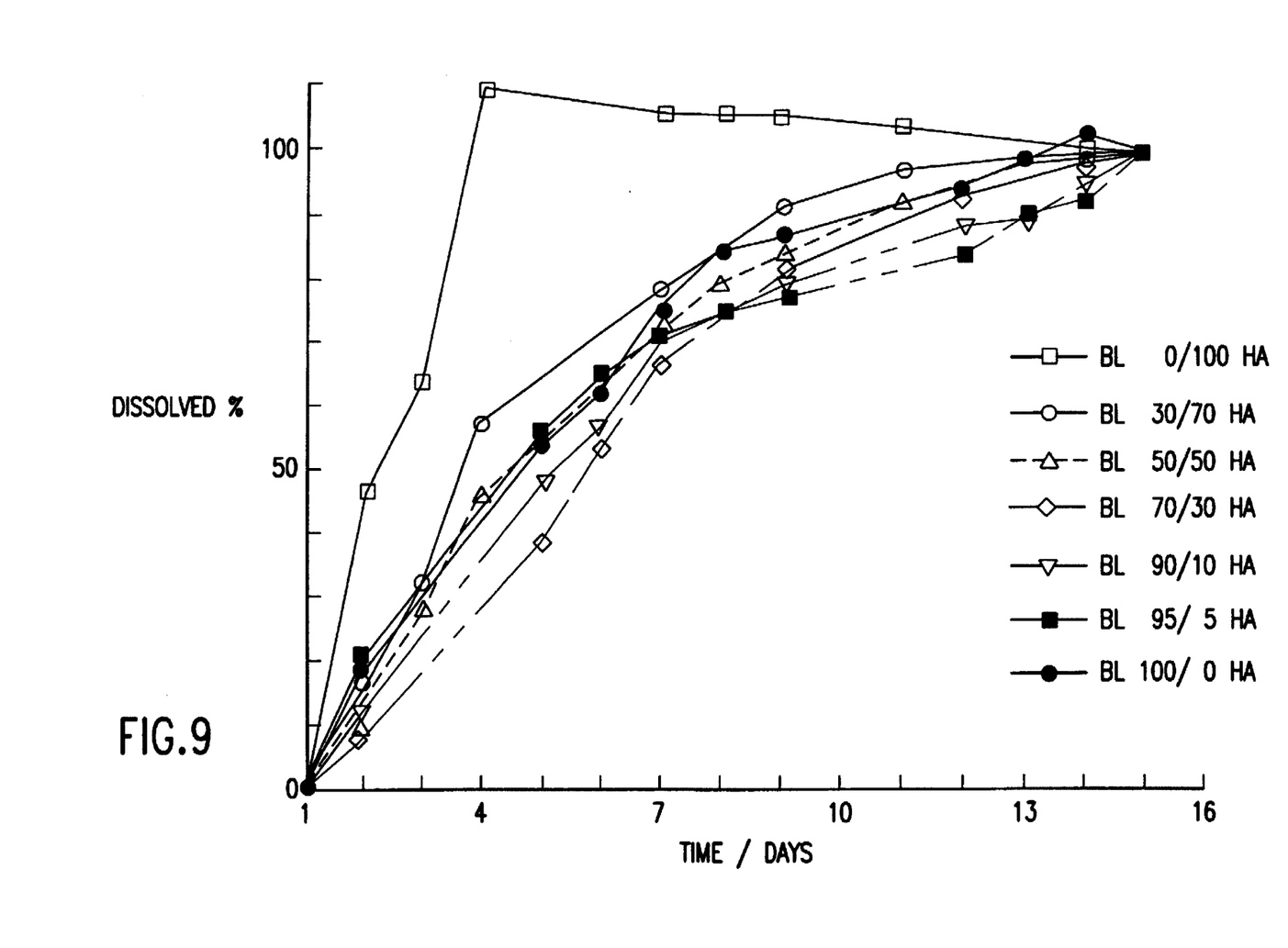
FIG. 9 The dissolution of selegiline hydrochloride as a function of time in phosphate buffer pH 7.4 (USP) from tablets comprising selegiline hydrochloride and the components of the bioceramic system. The tablets were pressed and then sintered. The tablets were impregnated with selegiline hydrochloride solution so that each tablet contained about 20 mg of the active compound. The components of the bioceramic system are presented in Table 8.

The dissolution of selegiline hydrochloride as a function of time in phosphate buffer pH 7.4 (USP) is presented in FIG. 9. The tablets were pressed and then sintered. The tablets were impregnated with selegiline hydrochloride solution so that each tablet contained about 20 mg of the active compound. The components of the bioceramic system are presented in Table 8. The dissolution was carried out as described in Experiment 1.

TABLE 8

| No. | bioactive glass/% | HA/% |
|---|---|---|
| 1 | 0 | 100 |
| 2 | 30 | 70 |
| 3 | 50 | 50 |
| 4 | 70 | 30 |
| 5 | 90 | 10 |
| 6 | 95 | 5 |
| 7 | 100 | 0 |

EXPERIMENT 10

Figure 10:
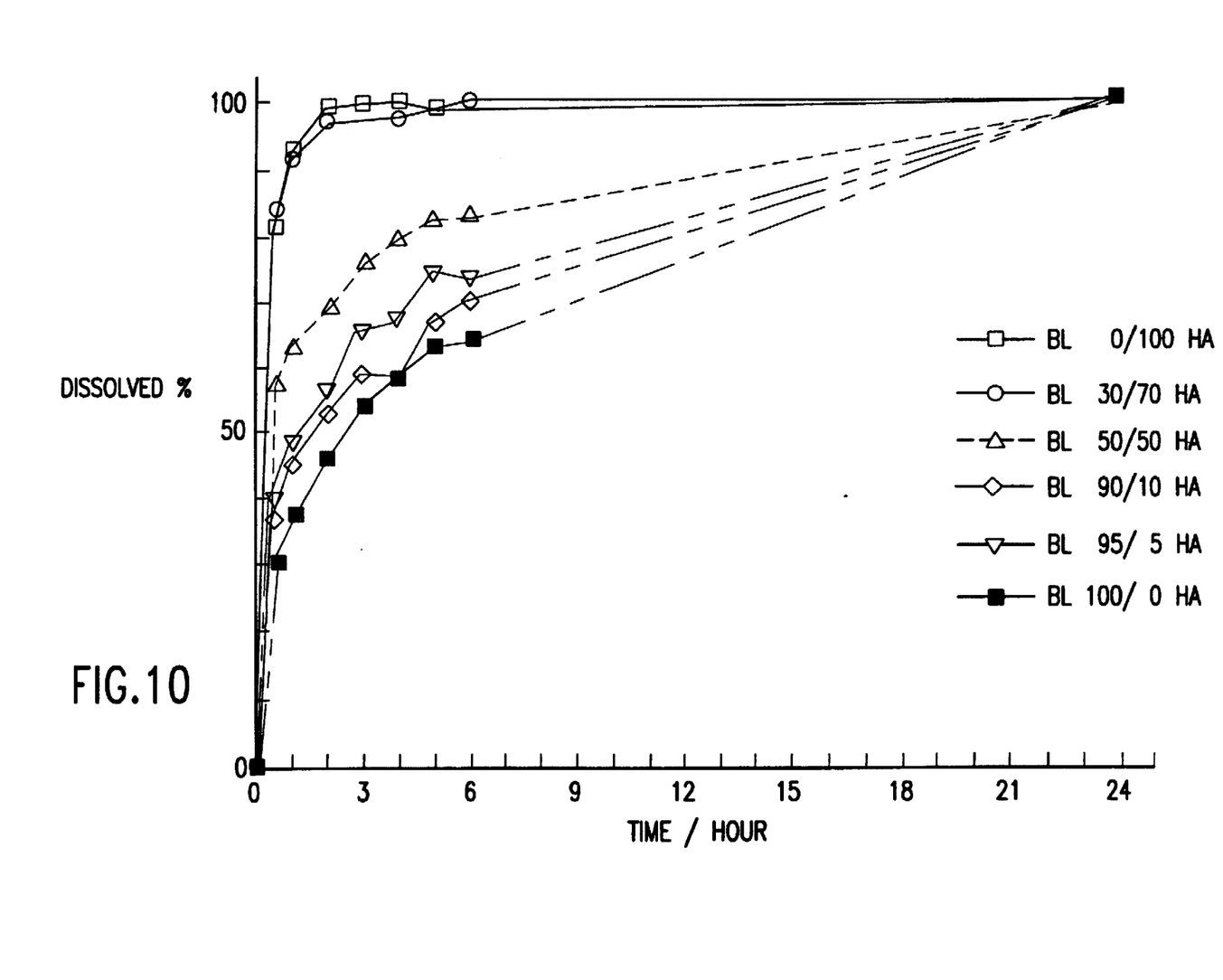
FIG. 10 The dissolution of selegiline hydrochloride as a function of time in pH 1.2 (0.1M hydrochloric acid) from tablets comprising selegiline hydrochloride and the components of the bioceramic system. The selegiline hydrochloride powder was mixed with the components of the bioceramic system before pressing. Each tablet contained about 20 mg of selegiline hydrochloride. The components of the bioceramic system are presented in Table 9.

The dissolution of selegiline hydrochloride as a function time in pH 1.2 (0.1M hydrochloric acid) is presented FIG. 10. The selegiline hydrochloride powder was mixed with the components of the bioceramic system before pressing. Each tablet contained about 20 mg of selegiline hydrochloride. The components of the system are presented in Table 9. The dissolution was carried out as described in Experiment 3.

TABLE 9

| No. | bioactive glass/% | HA/% | $H_2O$ |
|---|---|---|---|
| 1 | 0 | 100 | 2–4 drops |
| 2 | 30 | 70 | 2–4 drops |
| 3 | 50 | 50 | 2–4 drops |
| 4 | 90 | 10 | 2–4 drops |
| 5 | 95 | 5 | 2–4 drops |
| 6 | 100 | 0 | 2–4 drops |

EXPERIMENT 11

Figure 11:
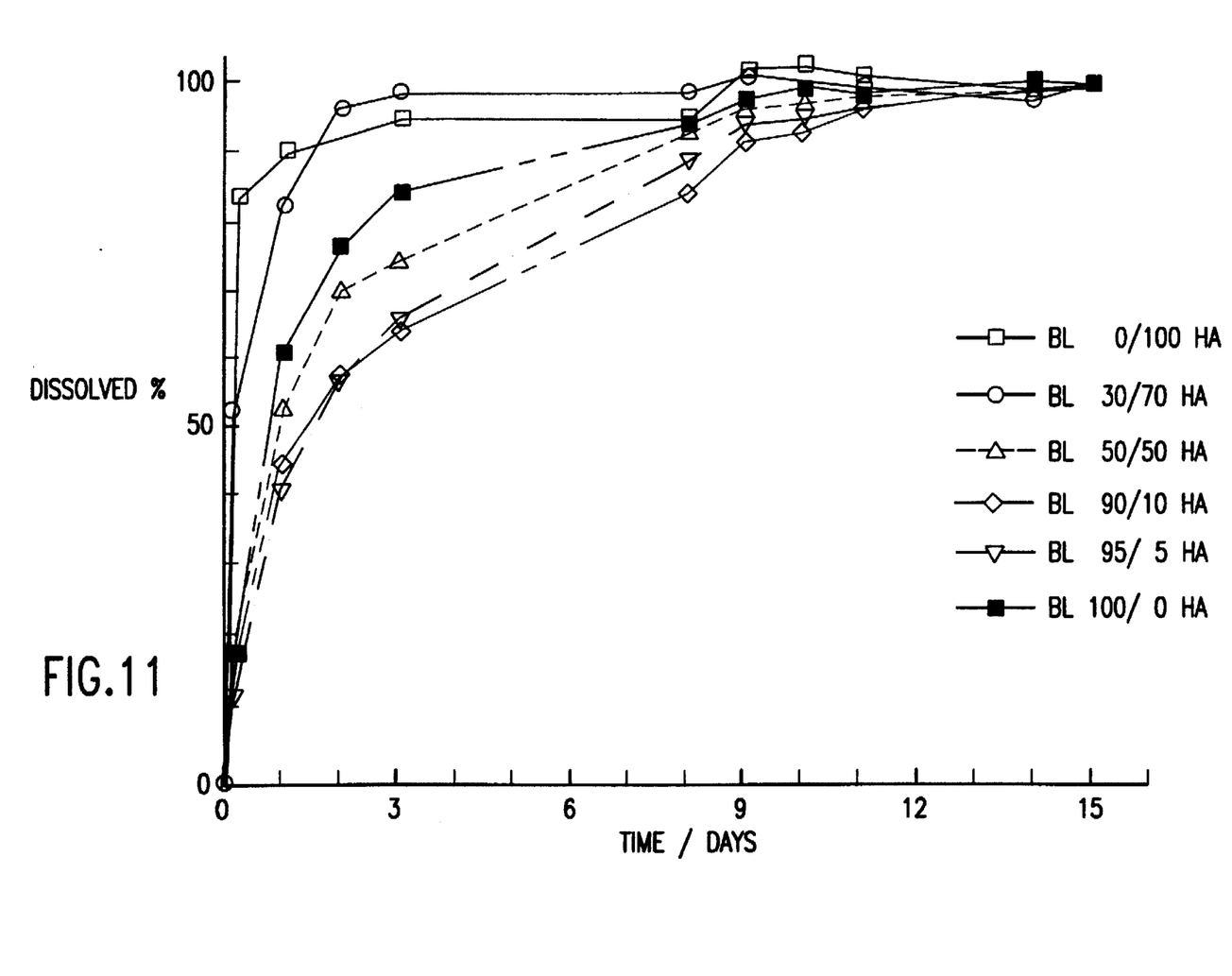
FIG. 11 The dissolution of selegiline hydrochloride as a function of time in phosphate buffer pH 7.4 (USP) from tablets comprising selegiline hydrochloride and the components of the bioceramic system. The selegiline hydrochloride powder was mixed with the components of the bioceramic system before pressing. Each tablet contained about 20 mg of selegiline hydrochloride. The components of the system are presented in Table 10.

The dissolution of selegiline hydrochloride as a function of time in phosphate buffer pH 7.4 (USP) is presented in FIG. 11. The selegiline hydrochloride powder was mixed with the components of the bioceramic system before pressing. Each tablet contained about 20 mg of selegiline hydrochloride. The components of the system are presented in Table 10. The dissolution was carried out as described in Experiment 1.

TABLE 10

| No. | bioactive glass/% | HA/% | H₂O |
|---|---|---|---|
| 1 | 0 | 100 | 2–4 drops |
| 2 | 30 | 70 | 2–4 drops |
| 3 | 50 | 50 | 2–4 drops |
| 4 | 90 | 10 | 2–4 drops |
| 5 | 95 | 5 | 2–4 drops |
| 6 | 100 | 0 | 2–4 drops |

EXPERIMENT 12

Figure 12:
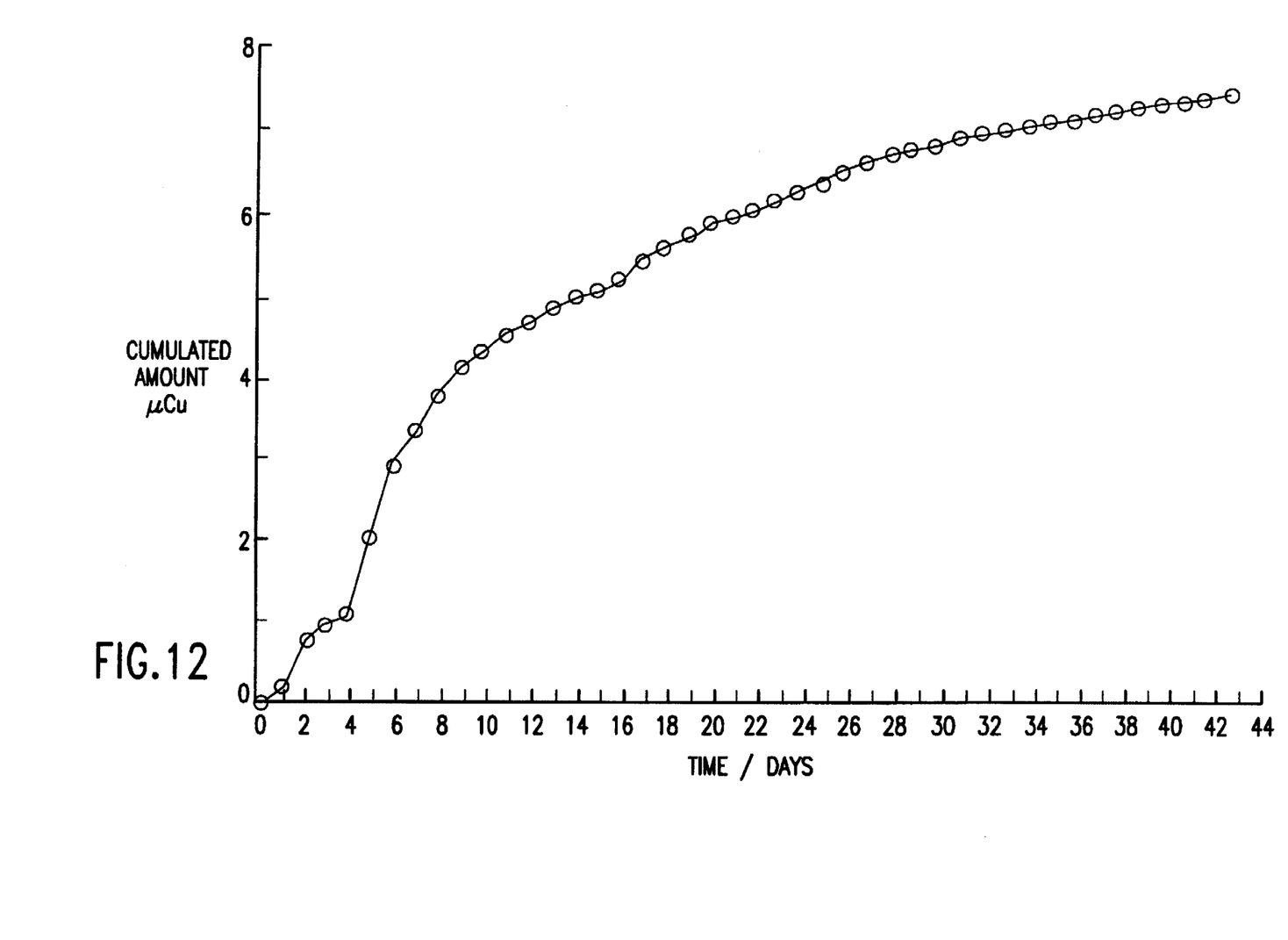
FIG. 12 The release of atipamezole from tablets comprising atipamezole and the components of the bioceramic system tested in vivo by using two Sprague-Dawley rats. The total radioactivity of the cumulated amount of atipamezole in urine as a function of time is presented.

The release of atipamezole from the bioceramic system was tested in vivo by using two Sprague-Dawley rats. Two tablets were made, one for each animal. The tablets consisted of 90% of bioactive glass, 10% of hydroxyapatite and 2–4 drops of water and was first pressed and then sintered at 650° C. for 10 minutes. The two tablets were first hot/dry air sterilized (140° C., 3 hours) and then the tablets were impregnated with tritiated atipamezole solution so that the radioactivity in each tablet was about 35.6 µCu. The tablets were implanted subcutaneously in the back of the rats. The urine of the rats was collected for 44 days and the radioactivity of the tritiated atipamezole in the urine was counted by liquid scintillation counter. The total radioactivity of the cumulated amount of atipamezole in urine as a function of time is presented in FIG. 12.

We claim:

1. A process for producing a resorbable bioceramic delivery device useful for in vivo delivery of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$ and CaO in the relative proportions within region A shown in FIG. 1 in Applicants' specification, said process comprising sintering (i) said hydroxyapatite and (ii) said bioactive glass, bioactive glass ceramic, or bioactive ceramic, and combining the product of the sintering step with (iii) at least one bioactive compound to produce said resorbable bioceramic delivery device.

2. The process of claim 1, wherein said resorbable bioceramic delivery device further comprises a matrix.

3. The process of claim 2, wherein said matrix is selected from the group consisting of gelatine and water.

4. The process of claim 2, wherein said matrix is waterglass.

5. The process of any of claims 1–4 wherein said resorbable bioceramic delivery device comprises one or more further calcium phosphate compounds, other than hydroxyapatite.

6. A process for producing a resorbable bioceramic delivery device useful for in vivo delivery of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification, said process comprising pressing a combination of (i) said hydroxyapatite, (ii) said bioactive glass, bioactive glass ceramic, or bioactive ceramic, sintering the product of the pressing step and combining the product of the sintering step with at least one bioactive compound to produce said resorbable bioceramic delivery device.

7. The process of claim 6, wherein said resorbable bioceramic delivery device further comprises a matrix.

8. The process of claim 7, wherein said matrix is selected from the group consisting of gelatine and water.

9. The process of claim 7, wherein said matrix is waterglass.

10. The process of any of claims 6–9 wherein said resorbable bioceramic delivery device comprises one or more further calcium phosphate compounds, other than hydroxyapatite.

11. The process of any of claims 1–4 or 6–9, wherein said bioactive compound is selected from the group consisting of a medicine, protein, and hormone.

12. The process of claim 11, wherein said bioactive compound is selected from the group consisting of anti-infectives, antibiotics, anti-virals, analgesics, anorexics, antihelminthics, parasiticides, anti-arthritics, anti-asthmatics, anti-convulsants, anti-depressants, anti-diabetics, anti-diarrheals, anti-histamines, anti-inflammatories, anti-migraines, anti-nauseants, anti-neoplastics, anti-cancers, anti-pruritics, anti-psychotics, anti-pryretics, anti-spasmodics, anti-cholingerics, sympathomimetics, xanthines, cardiovasculars, anti-arhythmics, anti-hypertensives, diuretics, vasodilators, central nervous system drugs, cough and cold preparations, decongestants, steroids, contraceptives, propyllactics, hypnotics, immunosuppressives, muscle relaxants, parasympatholytics, psychostimulants, sedatives, tranquilizers and cognitive dysfunction drugs.

13. The process of claim 11, wherein said bioactive compound is selegiline.

14. The process of claim 11, wherein said bioactive compound is methotrexate.

15. The process of claim 11, wherein said bioactive compound is nifedipine.

16. The process of claim 11, wherein said bioactive compound is atipamezole.

17. A process for producing a resorbable bioceramic delivery device useful for in vivo delivery of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification, said process comprising pressing a combination of (i) said hydroxyapatite, (ii) said bioactive glass, bioactive glass ceramic, or bioactive ceramic, and (iii) said bioactive compound to produce said resorbable bioceramic delivery device.

18. The process of claim 17, wherein said resorbable bioceramic delivery device further comprises a matrix.

19. The process of claim 18, wherein said matrix is selected from the group consisting of gelatine and water.

20. The process of claim 18, wherein said matrix is waterglass.

21. The process of any of claims 17–20, wherein said resorbable bioceramic delivery device comprises one or more further calcium phosphate compounds, other than hydroxyapatite.

22. A process for producing a resorbable bioceramic delivery device useful for in vivo delivery of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification, said process comprising pressing a combination of (i) said hydroxyapatite and (ii) said bioactive glass, bioactive glass ceramic, and bioactive ceramic, and combining the product of the pressing step with (iii) at least one bioactive compound to produce said resorbable bioceramic delivery device.

23. The process of claim 22, wherein said resorbable bioceramic delivery device further comprises a matrix.

24. The process of claim 23, wherein said matrix is selected from the group consisting of gelatine and water.

25. The process of claim 23, wherein said matrix is waterglass.

26. The process of any of claims 22–25, wherein said resorbable bioceramic delivery device comprises one or more further calcium phosphate compounds, other than hydroxyapatite.

27. The process of any of claims 17–20 or 22–25, wherein said bioactive compound is selected from the group consisting of a medicine, protein, and hormone.

28. The process of claim 27, wherein said bioactive compound is selected from the group consisting of anti-infectives, analgesics, anorexics, anthelminthics, parasiticides, anitiarthritics, antiasthmatics, anticonvulsants, antidepressants, antidiabetics, antidiarrheals, antihistamines, anti-inflammatories, antimigraines, antinauseants, antineoplastics, anti-cancer agents, antipruritics, antipsychotics, antipyretics, antispasmodics, anticholinergics, sympathomimetics, xanthine derivatives, cardiovascular agents, antiarrhythmics, antihypertensives, diuretics, vasodilators, CNS (=central nervous system) drugs, antiparkinsonism drugs, cough and cold drugs, decongestants, steroid contraceptives, prophylactics, hypnotics, immunosuppressives, muscle relaxants, parasympatholytics, psychostimulants, sedatives, tranquilizers, and cognitive dysfunction agents.

29. The process of claim 27, wherein said bioactive compound is selegiline.

30. The process of claim 27, wherein said bioactive compound is methotrexate.

31. The process of claim 27, wherein said bioactive compound is nifedipine.

32. The process of claim 27, wherein said bioactive compound is atipamezole.

33. A resorbable bioceramic delivery device useful for in vivo delivery of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification.

34. A pressed, resorbable bioceramic delivery device useful for in vivo delivery of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification.

35. A sintered, resorbable bioceramic delivery device useful for in vivo delivery of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification.

36. A pressed, sintered, and resorbable bioceramic delivery device useful for in vivo delivery of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification.

37. A bioceramic delivery device according to any one of claims 33–36 wherein the delivery device further comprises a matrix.

38. A bioceramic delivery device according to claim 37 wherein the matrix is gelatine and/or water.

39. A bioceramic delivery device according to claim 37 wherein the matrix is waterglass.

40. A bioceramic delivery device according to any one of claims 33–36 which further comprises one or more calcium phosphate compound other than hydroxyapatite.

41. A bioceramic delivery device according to claim 37 which further comprises one or more calcium phosphate compound other than hydroxyapatite.

42. The bioceramic delivery device of any of claims 33–36, wherein said bioactive compound is selected from the group consisting of a medicine, protein, and hormone.

43. The bioceramic delivery device of claim 42, wherein said bioactive compound is selected from the group consisting of anti-infectives, analgesics, anorexics, anthelminthics, parasiticides, antiarthritics, antiasthmatics, anticonvulsants, antidepressants, antidiabetics, antidiarrheals, antihistamines, anti-inflammatories, antimigraines, antinauseants, antineoplastics, anti-cancer agents, antipruritics, antipsychotics, antipyretics, antispasmodics, anticholinergics, sympathomimetics, xanthine derivatives, cardiovascular agents, antiarrhythmics, antihypertensives, diuretics, vasodilators, CNS (=central nervous system) drugs, antiparkinsonism drugs, cough and cold drugs, decongestants, steroid contraceptives, prophylactics, hypnotics, immunosuppressives, muscle relaxants, parasympatholytics, psychostimulants, sedatives, tranquilizers, and cognitive dysfunction agents.

44. The bioceramic delivery device of claim 42, wherein said bioactive compound is selegiline.

45. The bioceramic delivery device of claim 42, wherein said bioactive compound is methotrexate.

46. The bioceramic delivery device of claim 42, wherein said bioactive compound is nifedipine.

47. The bioceramic delivery device of claim 42, wherein said bioactive compound is atipamezole.

48. A monolithe, multiparticle system, whiskers system, fibrous system, tablet, pill, suppository, granule or suspension comprising a bioceramic delivery device as claimed in any one of claims 33–36.

49. A process for administering a bioactive compound to a subject to whom such administration is desired comprising administering a bioceramic delivery device as claimed in any one of claims 33–36, or a monolithe, multiparticle system, whiskers-like system, fibrous system, tablet, pill, suppository, granule or suspension comprising a bioceramic delivery device as claimed in claim 48.

50. A method of administering a bioceramic delivery device as claimed in any one of claims 33–36 which is implantation.

51. A pharmaceutical preparation comprising a resorbable bioceramic delivery device useful for in vivo delivery of a therapeutically effective amount of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification.

52. A pharmaceutical preparation comprising a pressed, resorbable bioceramic delivery device useful for in vivo delivery of a therapeutically effective amount of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification.

53. A pharmaceutical preparation comprising a sintered, resorbable bioceramic delivery device useful for in vivo delivery of a therapeutically effective amount of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification.

54. A pharmaceutical preparation comprising a pressed, sintered, and resorbable bioceramic delivery device useful for in vivo delivery of a therapeutically effective amount of a bioactive compound released from said device in vivo, which device comprises (i) hydroxyapatite, (ii) at least one of a bioactive glass, bioactive glass ceramic, or bioactive ceramic, and (iii) at least one bioactive compound, wherein said bioactive glass, bioactive glass ceramic, or bioactive ceramic comprises a ternary mixture of $SiO_2$, $Na_2O$, and CaO in the relative proportions within region A shown in FIG. 1 in Applicants' specification.

55. A pharmaceutical preparation according to any of claims 51–54 wherein said device further comprises a matrix.

56. A pharmaceutical preparation according to claim 55 wherein said matrix is gelatine and/or water.

57. A pharmaceutical preparation according to claim 55 wherein said matrix is waterglass.

58. A pharmaceutical preparation according to any one of claims 51–54 wherein said device further comprises one or more calcium phosphate compounds other than hydroxyapatite.

59. A pharmaceutical preparation according to claim 55 wherein said device further comprises one or more calcium phosphate compounds other than hydroxyapatite.

60. The pharmaceutical preparation of any of claims 51–54 wherein said bioactive compound is selected from the group consisting of a medicine, a protein, and a hormone.

61. The pharmaceutical preparation of claim 60 wherein said medicine, protein or hormone is selected from the group of agents consisting of anti-infectives, analgesics, anorexics, anthelminthics, parasiticides, antiartritics, antiasthmatics, anticonvulsants, antidepressants, antidiabetics, antidiarrheals, antihistamines, anti-inflammatory agents, antimigraines, antinauseants, antineoplastics, anti-cancer agents, antipruritics, antipsychotics, antipyretics, antispasmodics, anticholinergics sympathomimetics, xanthine derivatives, cardiovascular agents, antiarrhythmics, antihypertensives, diuretics, vasodilators, CNS (=central nervous system) drugs, antiparkinsonism drugs, cough and cold drugs, decongestants, steroid contraceptives, prophylactics, hypnotics, immunosuppressives, muscle relaxants, parasympatholytics, psychostimulants, sedatives, tranquilizers, and cognitive dysfunction agents.

62. The pharmaceutical preparation of claim 60 wherein said medicine is selegiline.

63. The pharmaceutical preparation of claim 60 wherein said medicine is methotrexate.

64. The pharmaceutical preparation of claim 60 wherein said medicine is nifedipine.

65. The pharmaceutical preparation of claim 60 wherein said medicine is atipamezole.

66. A monolithe, multiparticle system, whiskers system, fibrous system, tablet, pill, suppository, granule or suspension comprising said pharmaceutical preparation of any one of claims 51–54.

67. A process for administering a bioactive compound to a subject to whom such administration is desired comprising administering said preparation of any one of claims 51–54.

68. A process for administering a bioactive compound to a subject to whom such administration is desired comprising administering said preparation of claim 66.

69. A method of administering said preparation of any one of claims 51–54 wherein said method comprises implantation.

* * * * *